US011939633B2

(12) United States Patent
Jeong et al.

(10) Patent No.: US 11,939,633 B2
(45) Date of Patent: Mar. 26, 2024

(54) COTL1 PROTEIN INVOLVED IN MAINTAINING HOMEOSTASIS OF HEMATOPOIETIC STEM CELL, AND USE THEREOF

(71) Applicant: AJOU UNIVERSITY INDUSTRY-ACADEMIC COOPERATION FOUNDATION, Suwon-si (KR)

(72) Inventors: Seon-Yong Jeong, Yongin-si (KR); Eunkuk Park, Suwon-si (KR); Gijeong Kim, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 803 days.

(21) Appl. No.: 16/612,031

(22) PCT Filed: May 10, 2018

(86) PCT No.: PCT/KR2018/005343
§ 371 (c)(1),
(2) Date: Nov. 8, 2019

(87) PCT Pub. No.: WO2018/212503
PCT Pub. Date: Nov. 22, 2018

(65) Prior Publication Data
US 2020/0165674 A1 May 28, 2020

(30) Foreign Application Priority Data
May 19, 2017 (KR) .................. 10-2017-0062323

(51) Int. Cl.
C12N 15/113 (2010.01)
C12Q 1/6883 (2018.01)
G01N 33/68 (2006.01)

(52) U.S. Cl.
CPC .......... *C12Q 1/6883* (2013.01); *C12N 15/113* (2013.01); *G01N 33/6893* (2013.01); *C12N 2310/14* (2013.01); *C12Q 2600/136* (2013.01); *C12Q 2600/158* (2013.01); *G01N 2333/4703* (2013.01); *G01N 2500/00* (2013.01); *G01N 2800/22* (2013.01)

(58) Field of Classification Search
None
See application file for complete search history.

(56) References Cited

U.S. PATENT DOCUMENTS 9,081,013 B2 * 7/2015 Tanaka ............ G01N 33/57446
2009/0324618 A1 12/2009 Armstrong et al.
2012/0070450 A1 3/2012 Ishikawa et al.
2016/0032317 A1 2/2016 Rossi et al.

FOREIGN PATENT DOCUMENTS

CN 103667284 A 3/2014
KR 10-2016-0018525 A 2/2016
WO 2010/108126 A2 9/2010

OTHER PUBLICATIONS

Xia et al. Oncogene 37, 323,331 (Year: 2017).*
Miharada et al., "Dppa5 Improves Hematopoietic Stem Cell Activity by Reducing Endoplasmic Reticulum Stress", Cell Reports, vol. 7, No. 5, pp. 1381-1392, Jun. 12, 2014, 25 pages total.
Shanu et al., "The Role of Human Coactosin-Like Protein in Neurodegenerative Disorders", Biochemistry and Modern Applications, Dec. 31, 2017, vol. 1, Issue 1, PDF 107, pp. 20-24, 5 pages total.
Li et al., "Hematopoietic stem cells: cancer involvement and myeloid leukemia", European Review for Medical and Pharmacological Sciences, 2015, vol. 19, pp. 1829-1836, 8 pages total.
Gatta et al., "Early and sustained altered expression of aging-related genes in young 3xTg-AD mice", Cell Death and Disease, 2014, vol. 5, e1054, doi:10.1038/cddis.2014.11, 10 pages total.
Steward et al., "Haemopoietic stem cell transplantation for genetic disorder", Archives of Disease in Childhood, 2005, vol. 90, doi: 10.1136/adc.2005.074278, pp. 1259-1263, 6 pages total.
Rowley, "Molecular genetics in acute leukemia", Leukemia, 2000, vol. 14, No. 3, pp. 513-517, 5 pages total.
Tuerk et al., "Systematic Evolution of Ligands by Exponential Enrichment: RNA Ligands to Bacteriophage T4 DNA Polymerase", Science, vol. 249, Aug. 3, 1990, pp. 505-510, 7 pages total.
Park et al., "Effects of Dihydrophaseic Acid 3'-O-β-D-Glucopyranoside Isolated from *Lycii radicis* Cortex on Osteoblast Differentiation", Molecules, 2016, vol. 21, No. 1260, 13 pages total.
Ellington et al., "In vitro selection of RNA molecules that bind specific ligands", Nature, vol. 346, Aug. 30, 1990, pp. 818-822, 5 pages total.
Famulok et al., "Nucleic Acid Aptamers—From Selection in Vitro to Applications in Vivo", Accounts of Chemical Research, 2000, vol. 33, pp. 591-599, 9 pages total.
Wilson et al., "In Vitro Selection of Functional Nucleic Acids", Annu. Rev. Biochem, 1999, vol. 68, pp. 611-647, 37 pages total.

(Continued)

*Primary Examiner* — Brian Whiteman
(74) *Attorney, Agent, or Firm* — Sughrue Mion, PLLC

(57) ABSTRACT

A COTL1 gene or protein maintains and regulates the homeostasis of hematopoietic stem cells. A method of diagnosis and treatment of blood-related disease caused either by abnormalities in the homeostasis of hematopoietic stem cells, which result from a mutation in the COTL1 gene or a decrease in the expression of the COTL1 protein, or by an imbalance between the differentiation or proliferation and damage or death of hematopoietic stem cells, or by abnormalities in mitochondrial homeostasis are disclosed. The COTL1 gene or protein plays an important role in regulating mitochondrial morphology, and when it is knocked down, the number of hematopoietic stem cells decreases.

3 Claims, 15 Drawing Sheets
(13 of 15 Drawing Sheet(s) Filed in Color)
Specification includes a Sequence Listing.

(56) References Cited

OTHER PUBLICATIONS

Lim et al., "Modulation of Melanogenesis by Heme Oxygenase-1 via p53 in Normal Human Melanocytes", Chonnam Med J, 2016, vol. 52, pp. 45-52, 8 pages total.
Jin et al., "Transforming Growth Factor-β Stimulates p300-dependent RUNX3 Acetylation, Which Inhibits Ubiquitination-mediated Degradation", The Journal of Biological Chemistry, vol. 279, No. 28, Issue of Jul. 9, pp. 29409-29417, 2004, 10 pages total.
Kim et al., "Cyp1a reporter zebrafish reveals target tissues for dioxin", Aquatic Toxicology, vol. 134-135, 2013, pp. 57-65, 9 pages total.
International Searching Authority International Search Report dated Aug. 23, 2018 in International Application No. PCT/KR2018/005343.

\* cited by examiner

FIG. 4A
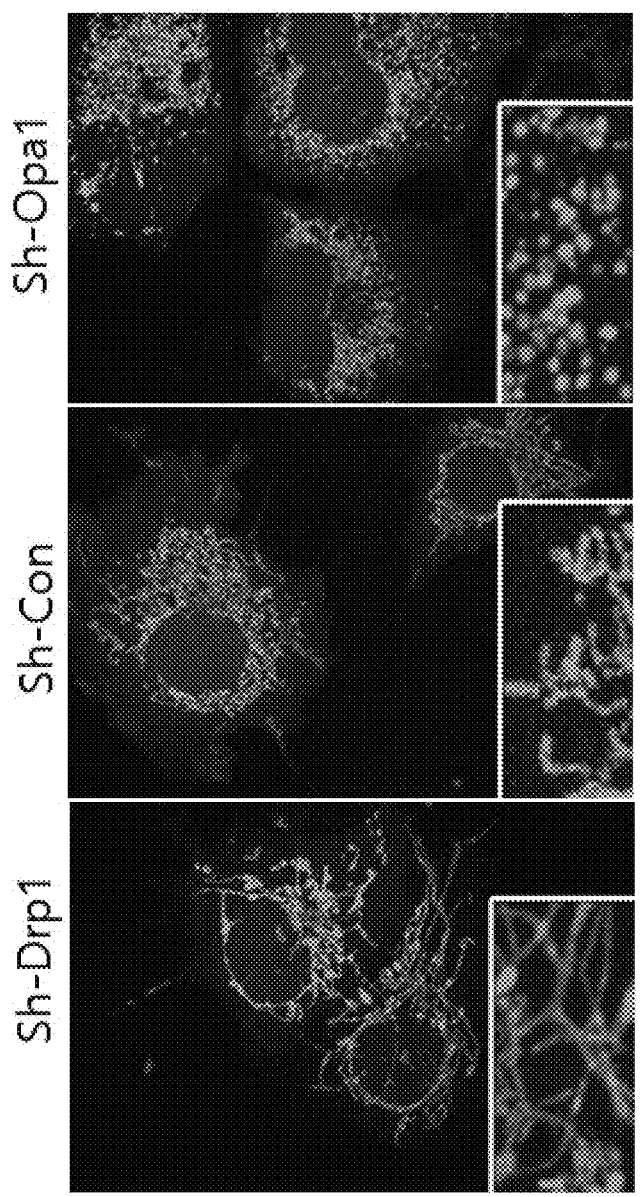
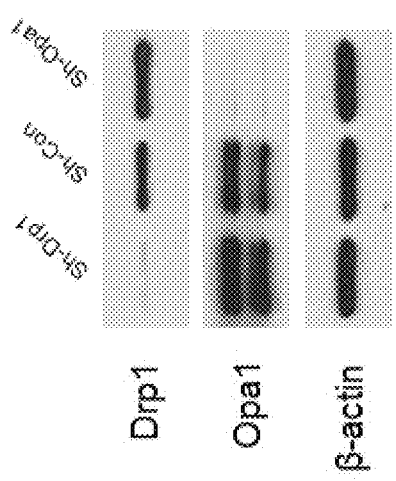

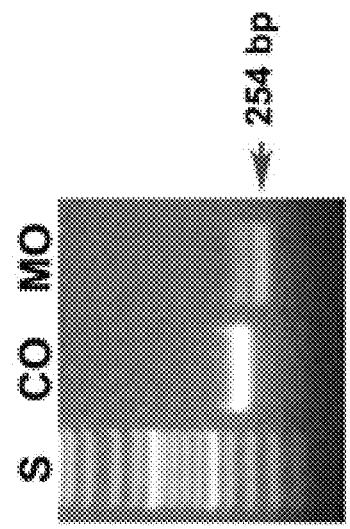
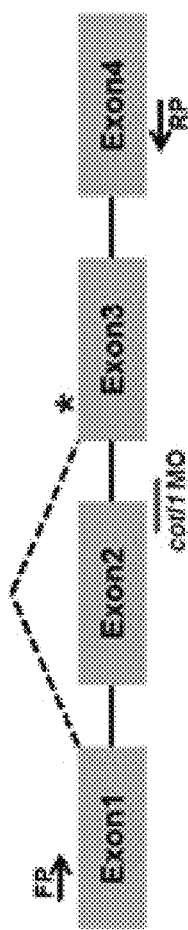
FIG. 7

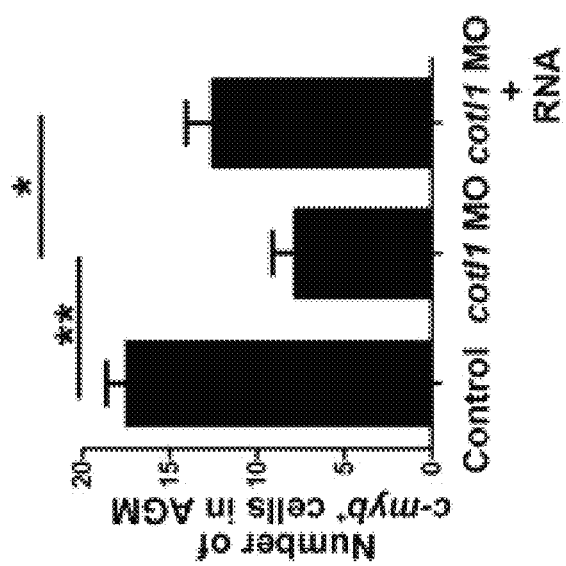
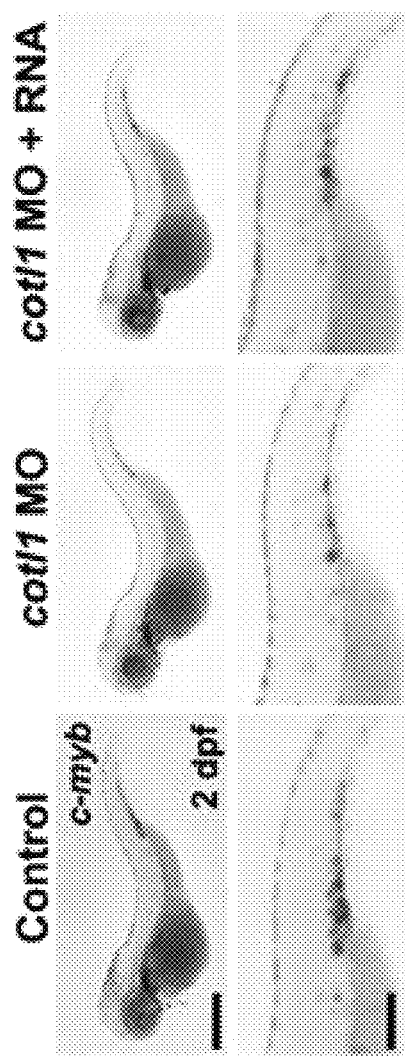
FIG. 8A

FIG. 9
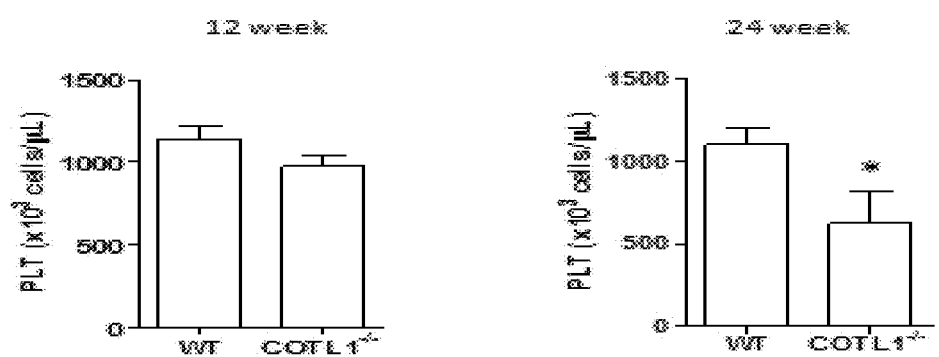
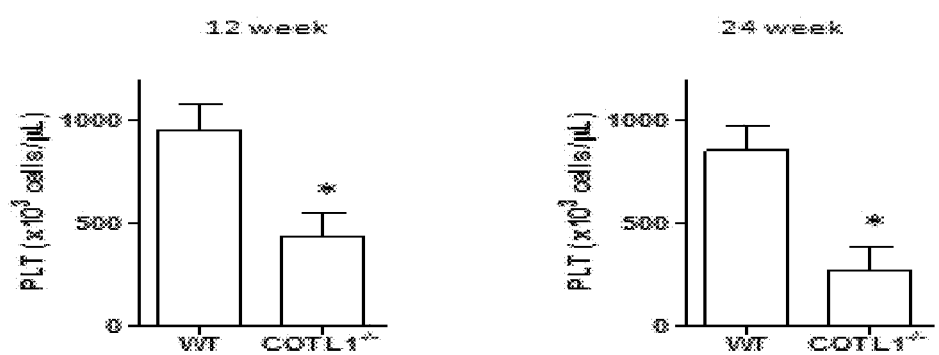

FIG. 10
Male
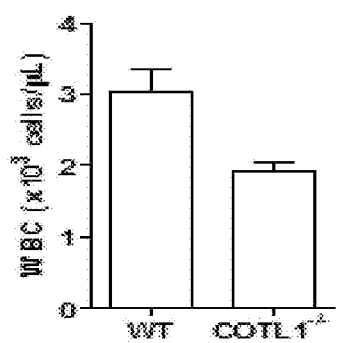
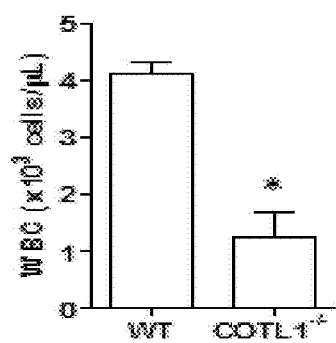
Female
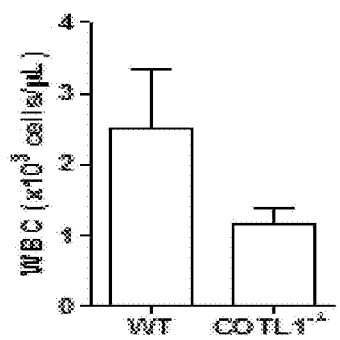
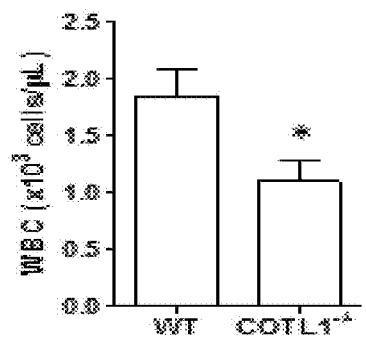

SEQUENCE LISTING

```
<160> NUMBER OF SEQ ID NOS: 8

<210> SEQ ID NO 1
<211> LENGTH: 29
<212> TYPE: DNA
<213> ORGANISM: Artificial Sequence
<220> FEATURE:
<223> OTHER INFORMATION: Opa1

<400> SEQUENCE: 1
gaugaaguua ucagucugag ccagguuac                                   29

<210> SEQ ID NO 2
<211> LENGTH: 29
<212> TYPE: DNA
<213> ORGANISM: Artificial Sequence
<220> FEATURE:
<223> OTHER INFORMATION: Dpr1

<400> SEQUENCE: 2
uucaauccgu gaugaguaug cuuuucuuc                                   29

<210> SEQ ID NO 3
<211> LENGTH: 32
<212> TYPE: DNA
<213> ORGANISM: Artificial Sequence
<220> FEATURE:
<223> OTHER INFORMATION: primer1

<400> SEQUENCE: 3
```

```
tcggcggatc caccatggca acacgaattg ac                                    32

<210> SEQ ID NO 4
<211> LENGTH: 29
<212> TYPE: DNA
<213> ORGANISM: Artificial Sequence
<220> FEATURE:
<223> OTHER INFORMATION: primer2

<400> SEQUENCE: 4
tagtcctcga gttattcagc ctgggcatc                                        29

<210> SEQ ID NO 5
<211> LENGTH: 25
<212> TYPE: DNA
<213> ORGANISM: Artificial Sequence
<220> FEATURE:
<223> OTHER INFORMATION: cotl1 MO

<400> SEQUENCE: 5
caagacaggt aaacagcact cacct                                            25

<210> SEQ ID NO 6
<211> LENGTH: 25
<212> TYPE: DNA
<213> ORGANISM: Artificial Sequence
<220> FEATURE:
<223> OTHER INFORMATION: control MO

<400> SEQUENCE: 6
cctcttacct ctgttacaat ttata                                            25

<210> SEQ ID NO 7
<211> LENGTH: 20
<212> TYPE: DNA
<213> ORGANISM: Artificial Sequence
<220> FEATURE:
<223> OTHER INFORMATION: primer3

<400> SEQUENCE: 7
gacaaagagg cttgcagaga                                                  20

<210> SEQ ID NO 8
<211> LENGTH: 20
<212> TYPE: DNA
<213> ORGANISM: Artificial Sequence
<220> FEATURE:
<223> OTHER INFORMATION: primer4

<400> SEQUENCE: 8
tggggtcgct gatcataaac                                                  20
```

COTL1 PROTEIN INVOLVED IN MAINTAINING HOMEOSTASIS OF HEMATOPOIETIC STEM CELL, AND USE THEREOF

CROSS REFERENCE TO RELATED APPLICATIONS

This application is a National Stage of International Application No. PCT/KR2018/005343, filed May 10, 2018, claiming priority to Korean Patent Application No. 10-2017-0062323, filed May 19, 2017.

SEQUENCE LISTING

The content of the electronically submitted sequence listing, file name: Q250958SequenceListingasfiled.txt; size: 1,813 bytes; and date of creation: Oct. 23, 2019, filed Nov. 8, 2019, is incorporated herein by reference in its entirety.

TECHNICAL FIELD

The present invention relates to the COTL1 gene or protein that maintains and regulates the homeostasis of hematopoietic stem cells, and more particularly to the diagnosis and treatment of blood-related disease caused either by abnormalities in the homeostasis of hematopoietic stem cells, which result from a mutation in the COTL1 gene or a decrease in the expression of the COTL1 protein, or by an imbalance between the differentiation or proliferation and damage or death of hematopoietic stem cells, or by abnormalities in mitochondrial homeostasis.

BACKGROUND ART

All types of blood cells are produced from multipotent cells, called hematopoietic stem cells (HSCs). The hematopoietic stem cells are cells that are capable of self-renewal and can proliferate and differentiate into various types of cells. In particular, in the early stages of hematopoiesis, pluripotent stem cells selectively differentiate into one type of cell among lymphoid progenitors and myeloid progenitors. The microenvironments in hematopoietic stem cells are important for differentiation and maturation of the cells. In particular, differentiation and proliferation of hematopoietic stem cells are greatly influenced by the types and amounts of about 20 hematopoietic growth factors.

Lymphoid progenitors produce B cells, T cells, natural killer (NK) cells, and plasma cells, and myeloid progenitors differentiate into erythrocytes, mast cells, and various leukocytes (basophils, neutrophils, eosinophils, and monocytes), and platelets. Cells that differentiated from hematopoietic stem cells are closely related to the immune system, detect and respond to a wide range of antigenic substances, including pathogens that invade the body, function to remove dead cells and heal wounds, and also form out body's defense system.

Hematopoietic stem cells are primarily present in bone marrow and are also present in small numbers in peripheral blood. Stimulation of hematopoietic growth factors increases hematopoietic stem cells in peripheral blood as a result of the migration, differentiation and proliferation of bone marrow hematopoietic stem cells. Since hematopoietic stem cells have self-renewal ability, the change in number and morphology of normal bone marrow cells are homeostatically maintained, even if blood cells are produced from hematopoietic stem cells and enter the peripheral blood.

It is known that hematopoietic stem cells produce 1,010 erythrocytes and 108 to 109 leukocytes per hour in a steady state and produce approximately $4 \times 10^{11}$ blood cells per day. In addition, hematopoietic stem cells have the ability to home to bone marrow, and this property allows for the transplantation of hematopoietic stem cells. Allogeneic hematopoietic stem cell transplantation has been performed for intractable blood-related diseases, such as malignant blood-related disease and severe aplastic anemia. In recent years, allogeneic hematopoietic stem cell transplantation has also been used as an effective therapy for various diseases, such as hereditary metabolic diseases and congenital immunodeficiency diseases (Steward C G et al., *Arch Dis Child.* 90(12):1259-63, 2005).

During hematopoiesis of blood cells that differentiated from hematopoietic stem cells, the differentiated cells at each stage maintain a balance between their proliferation or maturation and cell damage or death by energy homeostasis. Disruption of this homeostasis results in differentiation arrest or abnormal proliferation during hematopoiesis from hematopoietic stem cells to blood cells, causing intractable diseases such as intractable blood-related diseases and severe aplastic anemia. It may appear that these symptoms are caused either by abnormalities in colony stimulating factors (CSFs), which regulate the homeostasis of hematopoietic proliferation/differentiation in the lineage development of blood cells from hematopoietic stem cells, or by abnormalities in genes that control proliferation/differentiation signals in cells.

CSFs are commonly referred to as cytokines in the sense that they act on cell membrane receptors to alter cell function, and uncontrolled production of CSFs or overexpression of CSFs in cells can disrupt blood cell homeostasis. Such abnormalities in CSF have a significant effect on abnormal proliferation of blood cells, but do not directly explain the development of blood cancer. Thus, it has been gradually revealed that the direct and decisive cause of leukemia lies in genetic abnormalities that cause excessive proliferation of hematopoietic stem cells and an imbalance between intracellular signaling molecules (Rowley J D et al., *Leukemia.* 14(3):513-7, 2000).

The homeostasis of hematopoietic stem cells is maintained by the harmonious balance of blood-forming cells along with a balance between differentiation/proliferation and cell damage/death. Hematopoietic stem cells require a lot of energy when they differentiate, but resting hematopoietic stem cells are maintained at a low energy level by glycolytic metabolites. Thus, abnormalities in energy metabolism or reactive oxygen species (ROS) in hematopoietic stem cells are closely related to the differentiation of hematopoietic stem cells, and the maintenance of homeostasis of hematopoietic stem cells is closely related to the function of the mitochondria responsible for the homeostasis of energy metabolism. That is, it is expected that mitochondrial abnormalities will be highly related to diseases associated with human hematopoietic stem cell differentiation.

Accordingly, the present inventors have made extensive efforts to develop an agent for diagnosing and treating blood-related disease caused either by abnormalities in the homeostasis of hematopoietic stem cells, or by an imbalance between the differentiation or proliferation and damage or death of hematopoietic stem cells, or by abnormalities in mitochondrial homeostasis, and as a result, have found that the COTL1 gene plays an important role in the regulation of mitochondrial morphology and is involved in maintaining homeostasis, such as the number of hematopoietic stem cells, thereby completing the present invention.

DISCLOSURE OF INVENTION

Technical Problem

It is an object of the present invention to provide a method of providing information for diagnosing or predicting blood-related disease, in which the expression level of COTL1 gene or protein in an isolated biological sample is measured, and the measured expression level of the COTL1 gene or protein is compared with that in a control sample.

Another object of the present invention is to provide a pharmaceutical composition for preventing or treating blood-related disease, which contains, as an active ingredient, COTL1 protein or vector expressing COTL1 (mRNA of a COTL1 gene), and a pharmaceutical composition for preventing or treating blood-related disease, which contains, as an active ingredient, an inhibitor of the expression or activity of COTL1 protein.

Still another object of the present invention is to provide a method for preventing or treating blood-related disease, the method comprising administering a pharmaceutical composition which contains COTL1 protein or vector expressing COTL1 (mRNA of a COTL1 gene); or the method comprising administering a pharmaceutical composition which contains an inhibitor of the expression or activity of COTL1 protein.

Yet another object of the present invention is to provide a use of either a pharmaceutical composition which contains COTL1 protein or vector expressing COTL1 (mRNA of a COTL1 gene), or a pharmaceutical composition which contains an inhibitor of the expression or activity of COTL1 protein, for preventing or treating blood-related disease.

A further object of the present invention is to provide a use of either a pharmaceutical composition which contains COTL1 protein or vector expressing COTL1 (mRNA of a COTL1 gene), or a pharmaceutical composition which contains an inhibitor of the expression or activity of COTL1 protein, for manufacturing a medicament for preventing or treating blood-related disease.

A still further object of the present invention is to provide a method for screening an agent for treating blood-related disease, in which a cell is treated with a test substance, the expression level of COTL1 gene or protein in the cell is measured, and the test substance is selected if the measured expression level of the COTL1 gene or protein increased compared to that in a control not treated with the test substance.

Technical Solution

To achieve the above object, the present invention provides a method of providing information for diagnosing or predicting blood-related disease, the method comprising: (a) measuring the expression level of COTL1 gene or protein in an isolated biological sample; and (b) comparing the measured expression level of the COTL1 gene or protein with that in a control sample.

The present invention also provides a method for diagnosing or predicting blood-related disease, the method comprising: (a) measuring the expression level of COTL1 gene or protein in an isolated biological sample; and (b) comparing the measured expression level of the COTL1 gene or protein with that in a control sample.

The present invention also provides a pharmaceutical composition for preventing or treating blood-related disease, which contains, as an active ingredient, COTL1 protein or vector expressing COTL1 (mRNA of a COTL1 gene).

The present invention also provides a method for preventing or treating blood-related disease, the method comprising administering a pharmaceutical composition which contains, as an active ingredient, COTL1 protein or vector expressing COTL1 (mRNA of a COTL1 gene).

The present invention also provides a use of a pharmaceutical composition which contains, as an active ingredient, COTL1 protein or vector expressing COTL1 (mRNA of a COTL1 gene), for preventing or treating blood-related disease.

The present invention also provides a use of a pharmaceutical composition which contains, as an active ingredient, COTL1 protein or vector expressing COTL1 (mRNA of a COTL1 gene), for manufacturing a medicament for preventing or treating blood-related disease.

The present invention also provides a pharmaceutical composition for preventing or treating blood-related disease, which contains, as an active ingredient, an inhibitor of the expression or activity of COTL1 protein.

The present invention also provides a method for preventing or treating blood-related disease, the method comprising administering a pharmaceutical composition, which contains, as an active ingredient, an inhibitor of the expression or activity of COTL1 protein.

The present invention also provides a use of a pharmaceutical composition, which contains, as an active ingredient, an inhibitor of the expression or activity of COTL1 protein, for preventing or treating blood-related disease.

The present invention also provides a use of a pharmaceutical composition, which contains, as an active ingredient, an inhibitor of the expression or activity of COTL1 protein, for manufacturing a medicament for preventing or treating blood-related disease.

The present invention also provides a method for screening an agent for treating blood-related disease, comprising the steps of: (a) treating a cell with a test substance; (b) measuring the expression level of COTL1 gene or protein in the cell; and (c) selecting the test substance if the measured expression level of the COTL1 gene or protein increased compared to that in a control not treated with the test substance.

BRIEF DESCRIPTION OF THE DRAWINGS

The Application file contains at least one drawing executed in color. Copies of this application with the color drawings will be provided by the Office upon request and payment of the necessary fee.

FIG. 4A to 4C show the increase in migration of COTL1 to mitochondria due to a change in the intracellular distribution of COTL1, which results from an increase in mitochondrial length.

FIG. 7 shows cotl1 knockdown by morpholino RNA in zebrafish.

FIGS. 8A and 8B show a decrease in the number of hematopoietic stem cells in cotl1 knockdown zebrafish.

FIG. 9 shows platelet counts depending on the sex and age of cotl1 knockdown mice.

FIG. 10 shows leukocyte counts depending on the sex and age of cotl1 knockdown mice.

BEST MODE FOR CARRYING OUT THE INVENTION

Unless defined otherwise, all the technical and scientific terms used herein have the same meaning as those generally understood by one of ordinary skill in the art to which the invention pertains. Generally, the nomenclature used herein and the experiment methods, which will be described below, are those well known and commonly employed in the art.

In the present invention, it has been found that the key gene/protein COTL1 that changes its expression level when mitochondrial morphological abnormalities occur plays an important role in mitochondrial dynamics by regulating F-actin protein. In addition, it has also been found that knockdown of zebrafish cotl1 gene, a homologous gene of human COTL1, results in a definite decrease in the number of hematopoietic stem cells in the zebrafish developmental stage. That is, it could be confirmed that COTL1 is an important gene/protein which is involved in maintaining the homeostasis of hematopoietic stem cells during differentiation and proliferation.

Figure 3:
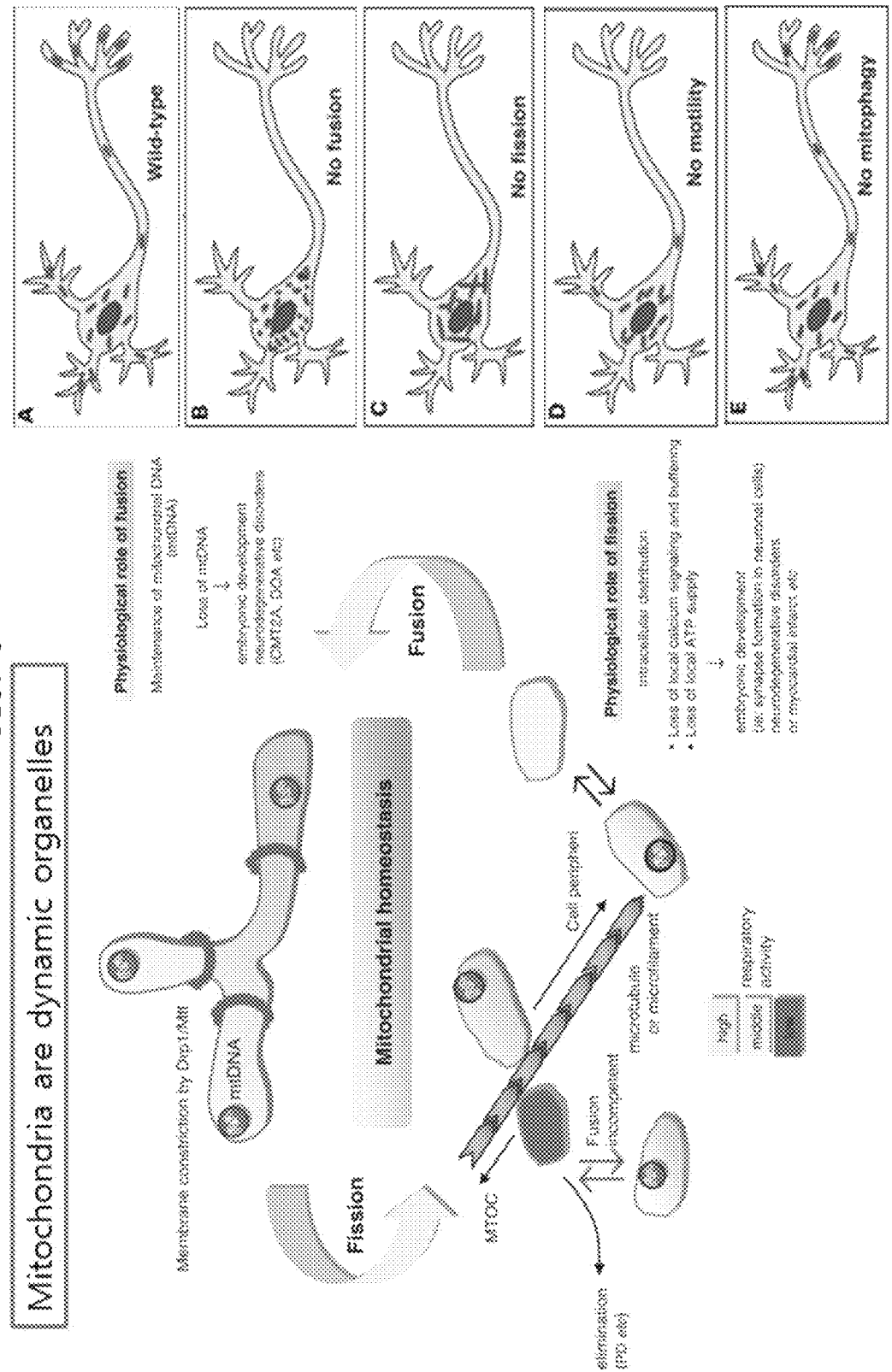
FIG. 3 shows a schematic view of mitochondrial dynamics and homeostasis maintenance mechanism.

Mitochondria play a pivotal role in the maintenance of various homeostasis of cells while playing as an intracellular energy plant responsible for the production of ATP necessary for cell life through an oxidative phosphorylation process in the cells. Mitochondria are highly dynamic organelles that constantly change their length and morphology. Mitochondria maintain the homeostasis of morphology, amount and number by repeating a fission process and a fusion process in which two or more mitochondria fuse into one. Through these fission and fusion processes, the homeostasis of intracellular energy metabolism is also maintained. This dynamic process of continuous fission and fusion of mitochondria is referred to as "mitochondrial dynamics" (FIG. 3).

Abnormalities in such mitochondrial dynamics are expected to be highly related to diseases associated with hematopoietic stem cell differentiation in humans. In recent years, studies on the effects of mitochondrial morphological abnormalities on abnormal differentiation and proliferation of hematopoietic stem cells have attracted a great deal of attention.

Hematopoietic stem cells are multipotent cells that produce all types of blood cells, even though only about 1% is present in blood. Cells differentiated from hematopoietic stem cells are responsible for our body's most important immune system. During hematopoiesis of blood cells differentiated from hematopoietic stem cells, the differentiated cells at each stage maintain a balance between their proliferation or maturation and cell damage or death by energy homeostasis, and the maintenance of homeostasis of hematopoietic stem cells is closely related to the function of mitochondria responsible for the homeostasis of energy metabolism. However, abnormalities in the homeostasis of hematopoietic stem cells cause abnormal differentiation and proliferation of hematopoietic stem cells and are associated with various types of blood-related diseases, including intractable blood-related diseases such as leukemia, aplastic anemia and blood cancer.

Figure 1:
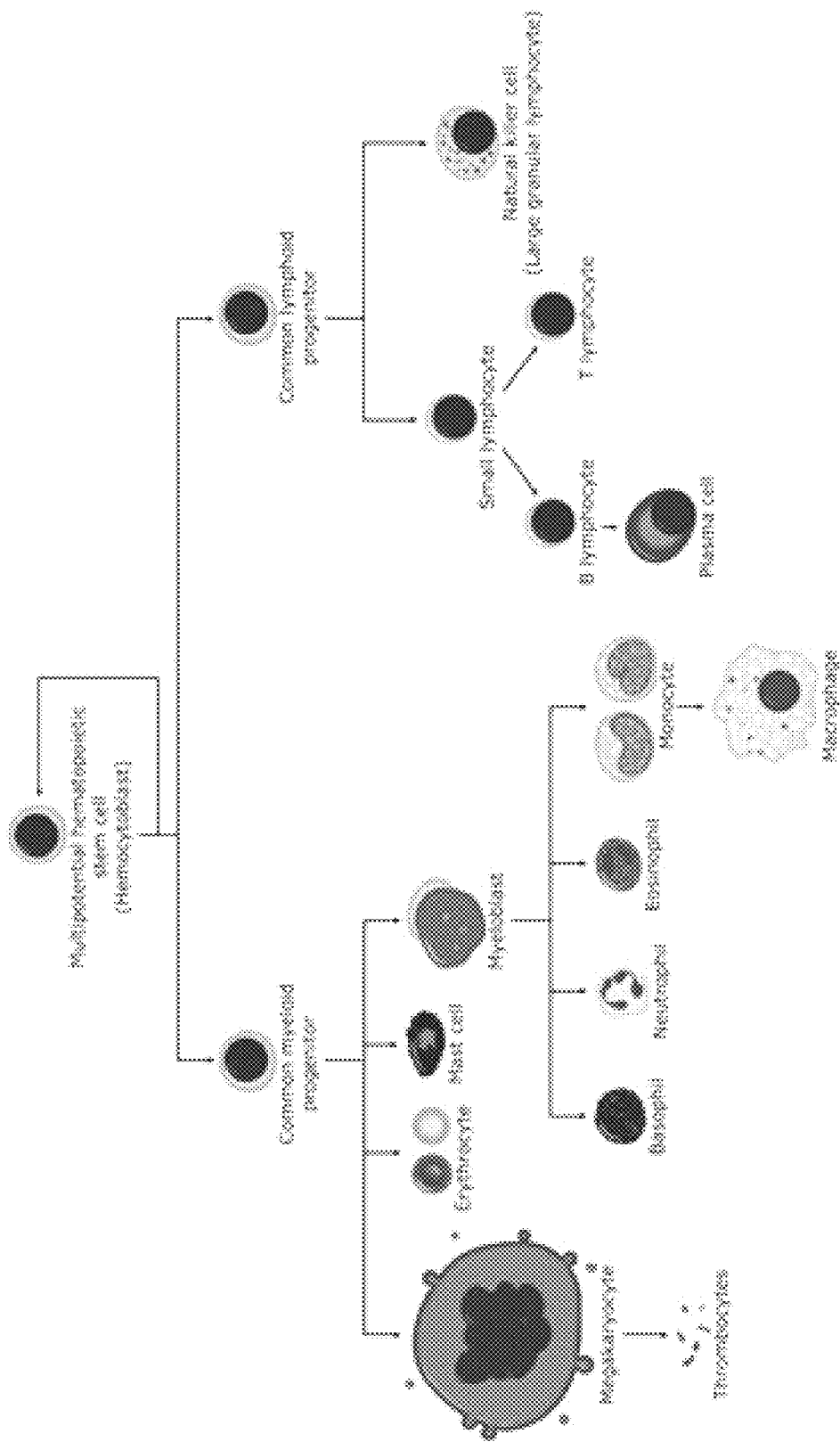
FIG. 1 shows a hematopoietic stem cell differentiation process.
Figure 2:
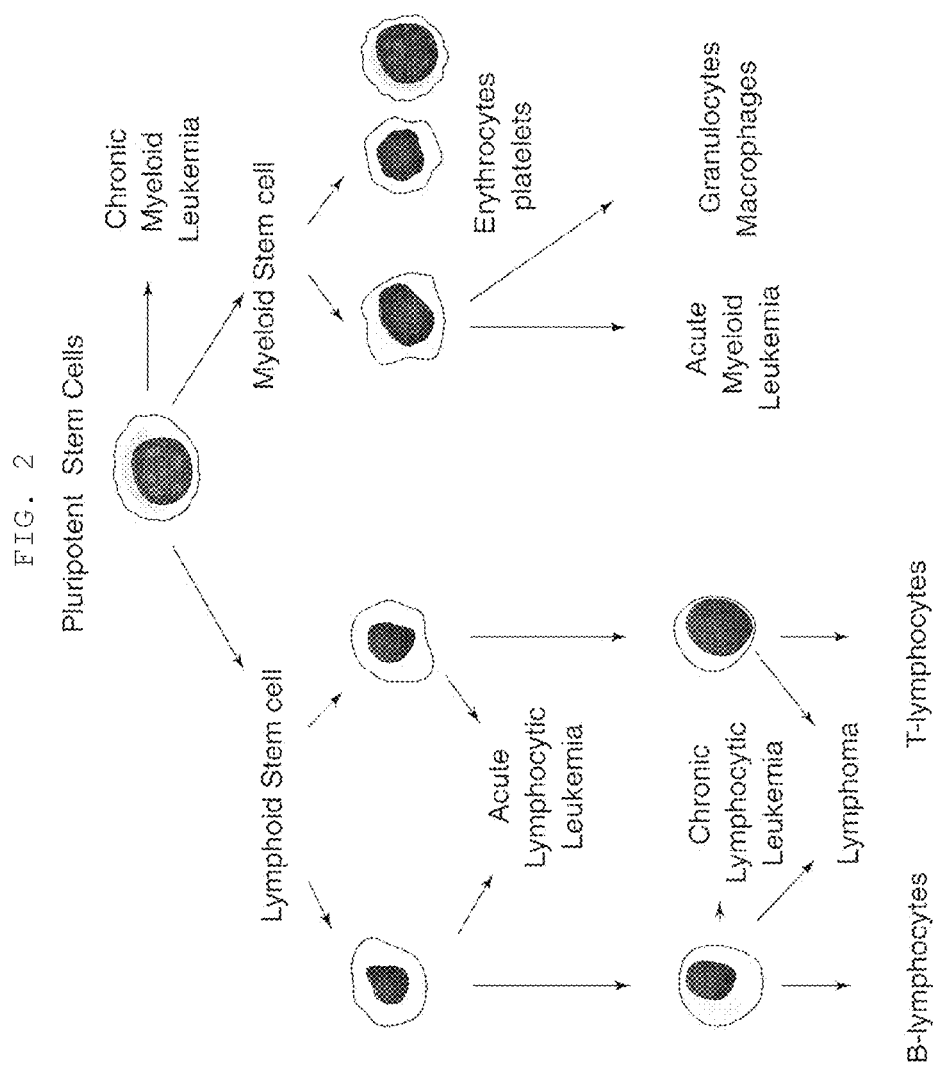
FIG. 2 shows the types of leukemia depending on the origin of hematopoietic stem cells.

Leukemia caused by abnormal proliferation of hematopoietic stem cells is divided into acute and chronic types according to the rate of exacerbation (differentiation and proliferation), and divided into myeloid and lymphoid types according to the origin of the cells. Specifically, the leukemia is frequently classified into the following four types (FIG. 2):

1) Acute myeloid leukemia: a malignant tumor developed in stem cells of myeloid leukocytes produced in the bone marrow.

2) Acute lymphoblastic leukemia: a disease developed in lymphocyte lineage cells in blood and bone marrow.

3) Chronic myeloid leukemia: a disease caused by abnormal proliferation of hematopoietic stem cells with the Philadelphia chromosome in bone marrow.

4) Chronic lymphocytic leukemia: a disease in which mature lymphocytes in blood significantly increase.

In the present invention, it has been found that COTL1, which binds to F-actin and is involved in mitochondrial morphological changes, plays an important role in maintaining the homeostasis of hematopoietic stem cells. In addition, it has been found that the number of hematopoietic stem cells in COTL1-knockdown zebrafish in the developmental stage significantly decreases. Therefore, it is expected that COTL1 knockdown and mutation will be closely related to the maintenance of hematopoietic stem cell homeostasis, and will be used to develop agents for the diagnosis and treatment of various blood-related diseases (leukemia, pernicious anemia, etc.) associated with hematopoietic stem cell homeostasis abnormalities, and thus will have very high medical and industrial applicability.

Therefore, in one aspect, the present invention is directed to a method of providing information for diagnosing or predicting blood-related disease, the method comprising: (a) measuring the expression level of COTL1 gene or protein in an isolated biological sample; and (b) comparing the measured expression level of the COTL1 gene or protein with that in a control sample.

In another aspect, the present invention is directed to a method for diagnosing or predicting blood-related disease, the method comprising: (a) measuring the expression level of COTL1 gene or protein in an isolated biological sample; and (b) comparing the measured expression level of the COTL1 gene or protein with that in a control sample.

In the present invention, in step (b), when the expression level of the COTL1 gene or protein decreases compared to that in the control sample, the isolated biological sample may be diagnosed or predicted to have the blood-related disease.

The blood-related disease is preferably selected from the group consisting of aplastic anemia, malignant lymphoma, acute myeloid leukemia, acute lymphoblastic leukemia, chronic myeloid leukemia, chronic liver disorders, renal failure, severe infections, myelopathic thrombocytopenia, idiopathic thrombocytopenic purpura (ITP), thrombasthenia, lymphocytopenia, neutropenia, monocytopenia, granulopenia, and myeloproliferative diseases, but is not limited as long as it is a disease caused by abnormalities in the homeostasis of hematopoietic stem cells, in which the homeostasis may mean that a balance between the differentiation or proliferation and damage or death of the cell is maintained. In addition, the blood-related disease may be caused by abnormalities in mitochondrial homeostasis, in which the homeostasis may mean that the mitochondria maintain their morphology, amount and number by repeating fission and fusion.

In the present invention, the sample is preferably selected from the group consisting of tissue, cell, blood, serum, plasma, saliva, phlegm, cerebrospinal fluid, sweat, urine, ascetic fluid, and peritoneal fluid, but is not limited thereto.

In the present invention, a substance for measuring the expression level of the COTL1 gene is preferably a primer pair capable of amplifying the COTL1 gene or a probe that binds specifically to the COTL1 gene, and a substance for measuring the expression level of the COTL1 protein is preferably an antibody or aptamer specific for the COTL1 protein, but the scope of the present invention is not limited thereto.

As used herein, the term "primer" refers to a nucleic acid sequence having a short free 3'-end hydroxyl group, which is a short nucleic acid sequence that may form a base pair with a complementary template and act as a start point for template strand replication. In the present invention, whether or not a desired product is produced may be determined by performing PCR amplification using the sense and antisense primers of a marker polynucleotide of the present invention, thereby predicting the prognosis of gastric cancer. PCR conditions and the lengths of the sense and antisense primers may be modified based on those known in the art.

As used herein, the term "probe" refers to a fragment of nucleic acid such as RNA or DNA, which can bind specifically to mRNA and is several nucleotides to several hundred nucleotides in length. The probe can determine the presence or absence of a specific mRNA, because it is labeled. The probe can be constructed as an oligonucleotide probe, a single-stranded DNA probe, a double-stranded DNA probe, an RNA probe or the like.

As used herein, the term "antibody" is a term known in the art and refers to a specific protein molecule that is directed against an antigenic site. For the purpose of the present invention, the antibody means an antibody that binds specifically to a marker gene. This antibody may be produced by cloning each gene into an expression vector according to a conventional method to obtain a protein encoded by the marker gene, and producing the antibody from the obtained protein. Here, a partial peptide obtainable from the protein is also included.

As used herein, the term "antibody" is intended to include all polyclonal antibodies, monoclonal antibodies and recombinant antibodies. The antibody refers to a specific protein molecule that is directed against an antigenic site.

In the present invention, the term "aptamer" is a single-stranded nucleic acid (DNA, RNA or modified nucleic acid) having the ability to bind to a target molecule with a high affinity and specificity while retaining its stable three-dimensional structure. Aptamers are comparable to monoclonal antibodies because of their ability to bind to target molecules with a characteristic high affinity (usually a pM level) and specificity, and have a high potential as alternative antibodies, especially as "chemical antibodies". In the present invention, the aptamer is a single-stranded DNA or RNA molecule, and may be obtained by isolating an oligomer, which binds to a specific chemical or biological molecule with a high affinity and selectivity, by an evolutionary engineering method called SELEX (systematic evolution of ligands by exponential enrichment), using an oligonucleotide library (C. Tuerand L. Gold, *Science* 249, 505-510, 2005; A. D. Ellington and J. W. Szostak, *Nature* 346, 818-822, 1990; M. Famulok, et. al., *Acc. Chem. Res.* 33, 591-599, 2000; D. S. Wilson and Szostak, *Annu. Rev. Biochem.* 68, 611-647, 1999). The aptamer may bind specifically to a target and regulate the activity of the target. For example, it may block the functionality of the target by binding to the target.

In the present invention, the measurement of the expression level of COTL1 gene or protein preferably uses any one selected from the group consisting of reverse transcription polymerase chain reaction (RT-PCR), competitive RT-PCR, real-time RT-PCR, RNase protection assay (RPA), northern blotting, DNA chip assay, Western blotting, enzyme linked immunosorbent assay (ELISA), Radioimmunoassay (RIA), radial immunodiffusion, Ouchterlony immunodiffusion, rocket immunoelectrophoresis, immunohistochemical staining, immunoprecipitation assay, complement fixation assay, fluorescence-activated cell sorter analysis (FACS), and protein chip technology assay, but not limited thereto.

In still another aspect, the present invention is directed to a pharmaceutical composition for preventing or treating blood-related disease, which contains, as an active ingredient, COTL1 protein or vector expressing COTL1 (mRNA of a COTL1 gene).

In yet another aspect, the present invention is directed to a method for preventing or treating blood-related disease, the method comprising administering a pharmaceutical composition which contains COTL1 protein or vector expressing COTL1 (mRNA of a COTL1 gene).

In a further aspect, the present invention is directed to a use of a pharmaceutical composition which contains COTL1 protein or vector expressing COTL1 (mRNA of a COTL1 gene), for preventing or treating blood-related disease.

In a still further aspect, the present invention is directed to a use of a pharmaceutical composition which contains COTL1 protein or vector expressing COTL1 (mRNA of a COTL1 gene), for manufacturing a medicament for preventing or treating blood-related disease.

In the present invention, the blood-related disease is preferably selected from the group consisting of aplastic anemia, malignant lymphoma, chronic liver disorders, renal failure, severe infections, myelopathic thrombocytopenia, idiopathic thrombocytopenic purpura (ITP), thrombasthenia, lymphocytopenia, neutropenia, monocytopenia, granulopenia, and myeloproliferative diseases, but is not limited as long as it is a disease caused either by abnormalities in the homeostasis of hematopoietic stem cells, or by an increase in the number of normal hematopoietic stem cells.

In addition, the homeostasis may mean that a balance between the differentiation or proliferation and damage or death of the cell is maintained, and expression of the COTL1 protein or gene can increase the number of normal hematopoietic stem cells, thereby treating blood-related disease in which the number of hematopoietic stem cells decrease.

In a yet further aspect, the present invention is directed to a pharmaceutical composition for preventing or treating blood-related disease, which contains, as an active ingredient, an inhibitor of the expression or activity of COTL1 protein.

In another further aspect, the present invention is directed to a method for preventing or treating blood-related disease, the method comprising administering a pharmaceutical composition, which contains an inhibitor of the expression or activity of COTL1 protein.

In another still further aspect, the present invention is directed to a use of a pharmaceutical composition, which contains an inhibitor of the expression or activity of COTL1 protein, for preventing or treating blood-related disease.

In another yet further aspect, the present invention is directed to a use of a pharmaceutical composition, which contains an inhibitor of the expression or activity of COTL1 protein, for manufacturing a medicament for preventing or treating blood-related disease.

In the present invention, the blood-related disease is preferably selected from the group consisting of acute myeloid leukemia, acute lymphoblastic leukemia, chronic myeloid leukemia, and chronic lymphocytic leukemia, but the blood-related disease is not particularly limited thereto as long as it is a blood-related disease caused either by abnormalities in the homeostasis of hematopoietic stem cells, or by an increase in abnormal proliferation of hematopoietic stem cells.

In addition, the homeostasis may mean that a balance between the differentiation or proliferation and damage or death of the cell is maintained, and abnormalities in the homeostasis of hematopoietic stem cells cause abnormal differentiation and proliferation of hematopoietic stem cells, thereby inducing intractable blood-related diseases such as leukemia. Thus, since abnormal proliferation of abnormal hematopoietic stem cells can be inhibited using an inhibitor of the expression or activity of the COTL1 protein, the use of an inhibitor of the expression or activity of the COTL1 protein in leukemia can reduce the number of abnormal hematopoietic stem cells and inhibit abnormal proliferation of hematopoietic stem cells.

In the present invention, the inhibitor may be any one selected from the group consisting of an antisense nucleotide, a small interfering RNA (siRNA) and a short hairpin RNA (shRNA), which binds complementarily to the mRNA of the COTL1 gene, and an aptamer, an antibody and a small molecule, which binds complementarily to the COTL1 protein.

The pharmaceutical composition according to the present invention may further comprise a suitable carrier, excipient or diluent that is generally used in the preparation of pharmaceutical compositions. Specifically, the pharmaceutical composition can be formulated according to a conventional method. For example, it may be formulated in the form of powders, granules, tablets, capsules, suspensions, emulsions, syrups, aerosols, and the like for oral applications, agents for external applications, suppositories, and sterile injection solutions. Carriers, excipients and diluents that can be contained in the pharmaceutical composition according to the present invention include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, and mineral oil. The pharmaceutical composition according to the present invention is formulated using diluents or excipients, such as fillers, extenders, binders, wetting agents, disintegrants or surfactants, which are commonly used. Solid formulations for oral administration include tablets, pills, powders, granules, capsules, etc. Such solid formulations are prepared by mixing the composition of present invention with at least one excipient, such as starch, calcium carbonate, sucrose, lactose, gelatin, etc. In addition to simple expedients, lubricants such as magnesium stearate, talc, etc. may also be added. Liquid formulations for oral administration, such as suspensions, internal solutions, emulsions, syrups, etc., may include simple diluents, e.g., water and liquid paraffin, as well as various excipients, e.g., wetting agents, sweeteners, aromatics, preservatives, etc. Formulations for parenteral administration include sterilized aqueous solutions, non-aqueous solvents, suspensions, emulsions, lyophilized agents, and suppositories. Non-aqueous solvents and suspensions may be prepared using propylene glycol, polyethylene glycol, vegetable oils such as olive oil, or injectable esters such as ethyloleate. As a base for suppositories, Witepsol, Macrogol, Tween 61, cacao fat, laurin fat, glycerogelatin, etc. may be used.

In an embodiment of the present invention, the formulations may be contained in the pharmaceutical composition of the present invention in an amount of 0.0001 wt % to 50 wt %, preferably 0.001 wt % to 10 wt %, based on the total weight of the final composition, but the amount of the formulations is not particularly limited thereto.

The pharmaceutical composition of the present invention may be administered in a pharmaceutically effective amount. As used herein, the term "pharmaceutically effective amount" refers to an amount sufficient for the treatment or prevention of diseases at a reasonable benefit/risk ratio applicable for medical treatment or prevention, and the level of the effective dosage may be determined based on factors including severity of disease, drug activity, a patient's age, weight, health conditions, sex, and drug sensitivity, duration of administration, administration route and dissolution rate, duration of treatment, factors including drugs to be used simultaneously in combination, and other factors well known in the medical field. The pharmaceutical composition of the present invention may be administered as an individual therapeutic agent, in combination with other therapeutic agents, or sequentially or simultaneously with conventional therapeutic agents. The composition may be administered once or multiple times. It is important to administer the composition in the minimum amount that can exhibit the maximum effect without causing side effects, in view of all the above-described factors.

The dose of the pharmaceutical composition of the present invention can be determined by a person skilled in the art in view of use purpose, severity of disease, a patient's age, body weight, sex and anamnesis, or the types of a substance used as an active ingredient. For example, the pharmaceutical composition of the present invention may be administered to mammals including humans at a daily dose of from 10 mg/kg to 100 mg/kg, and more preferably 10 mg/kg to 30 mg/kg. The composition of the present invention may be administered once or three times per day, or may be administered in multiple divided doses per day, but the frequency of administration is not particularly limited thereto.

As used herein, the term "preventing/prevention" refers to all kinds of actions associated with the inhibition or delay of the onset of blood tumors by administering the pharmaceutical composition according to the present invention.

As used herein, the term "treating/treatment" refers to all kinds of actions associated with the improvements in symptoms of blood tumors or the beneficial alteration of blood tumors by administering the administration of the composition.

As used herein, the term "administration" refers to the introduction of the pharmaceutical composition of the present invention to a subject by any appropriate method. The pharmaceutical composition of the present invention may be administered via various oral and parenteral routes as long as the pharmaceutical composition can arrive at a target tissue.

The pharmaceutical composition of the present invention may be administered through any general route, as long as it can reach a desired tissue. The composition of the present invention can be administered intraperitoneally, intravenously, intramuscularly, subcutaneously, transdermally, orally, intranasally, intrapulmonarily or intrarectally depending on the purpose or necessity, but is not limited thereto. In addition, the pharmaceutical composition of the present invention may also be administered by any device that can deliver the active ingredient into target cells.

In another yet further aspect, the present invention is directed to a method for screening an agent for treating blood-related disease, comprising the steps of: (a) treating a cell with a test substance; (b) measuring the expression level of COTL1 gene or protein in the cell; and (c) selecting the test substance if the measured expression level of the COTL1 gene or protein increased compared to that in a control not treated with the test substance.

In the present invention, the cell may have introduced therein COTL1 gene.

The term "test substance" used herein when referring to the screening method of the present invention refers to an unknown candidate substance that is used in screening to examine whether it affects the expression level of the gene, the level of the protein or the activity of the protein.

In the present invention, the blood-related disease is preferably selected from the group consisting of aplastic anemia, malignant lymphoma, acute myeloid leukemia, acute lymphoblastic leukemia, chronic myeloid leukemia, chronic liver disorders, renal failure, severe infections, myelopathic thrombocytopenia, idiopathic thrombocytopenic purpura (ITP), thrombasthenia, lymphocytopenia, neutropenia, monocytopenia, granulopenia, and myeloproliferative diseases, but is not limited thereto.

In the present invention, the measurement of the expression level of COTL1 gene or protein preferably uses any one selected from the group consisting of reverse transcription polymerase chain reaction (RT-PCR), competitive RT-PCR, real-time RT-PCR, RNase protection assay (RPA), northern blotting, DNA chip assay, Western blotting, enzyme linked immunosorbent assay (ELISA), Radioimmunoassay (RIA), radial immunodiffusion, Ouchterlony immunodiffusion, rocket immunoelectrophoresis, immunohistochemical staining, immunoprecipitation assay, complement fixation assay, fluorescence-activated cell sorter analysis (FACS), and protein chip technology assay, but not limited thereto.

EXAMPLES

Hereinafter, the present invention will be described in further detail with reference to examples. It will be obvious to a person having ordinary skill in the art that these examples are for illustrative purposes only and are not to be construed to limit the scope of the present invention.

Antibodies

Anti-Cotl1 (Abcam, T3481), anti-F-actin (Abcam, ab205), anti-Drp1 (BD Transduction Laboratories, 611112), anti-CoxIV (Abcam.Ab135711), anti-beta actin (Santa Cruz, sc-1616), anti-GAPDH (Santa Cruz, sc-365062), anti-Lamin B1 (Abcam 6581-1), anti-Opa1 (BD Transduction Laboratories, 612607)

Example 1: Construction of Three Types of HeLa Cells Having Different Mitochondrial Lengths Human full-length Cotl1 was cloned into each of pEGFP-N1, paGFP-N1, pmCherry-N1, pcDNA3.1 and pCMV-Mcy-Tag 3 according to the manufacturer's instruction, and then plasmids with induced point mutations were constructed using a QuickChange mutagenesis kit (Stratagene, Santa Clara, CA). Mito-GFP and DsRed2-Mito plasmids were received from Richard Youle (National Institute Health, Bethesda, MD), and GFP-UtrCH (Plasmid #26737) was purchased from Addgene.

The Hela cell line was cultured in DMEM medium containing 10% FBS, penicillin (100 U/mL) and streptomycin (100 μg/mL), and then transfected by Lipofectamine 2000 (Invitrogen) with each of the constructed plasmids in OPTi-MEM medium (Invitrogen) in a 6-well dish ($2\times10^5$ cells/well) according to the manufacturer's instruction.

After three types of HeLa cells (shDrp1, shRNA control, shOpa1) with different mitochondrial lengths were artificially constructed by genetic engineering according to the above-described method, mitochondrial morphology was observed with a confocal microscope (FIG. 4a). For the red channel (Mitotracker or DsRed2-Mito), maximum intensity projections were merged. 25 to 40 mitochondria per cell were clearly selected, and the length of the mitochondria was measured using Nikon Elements or Metamorph software.

Example 2: Mitochondrial Length Due to Change in Intracellular Distribution of COTL1

2-1: Distribution of COTL1 in Cells with Different Mitochondrial Lengths

The cells ($2.5\times10^6$ cells) constructed in Example 1 were cultured in two 100-mm dishes, and then the cytosolic, nuclear and mitochondrial fractions were isolated therefrom using a cell fractionation kit (Abcam, ab109719) according to the manufacturer's instruction. Cox IV (Abcam), Lamin-B1 (Abcam), GAPDH (Santa Cruz) were used as mitochondrial, nuclear and cytosolic loading controls, respectively.

Figure 4B:
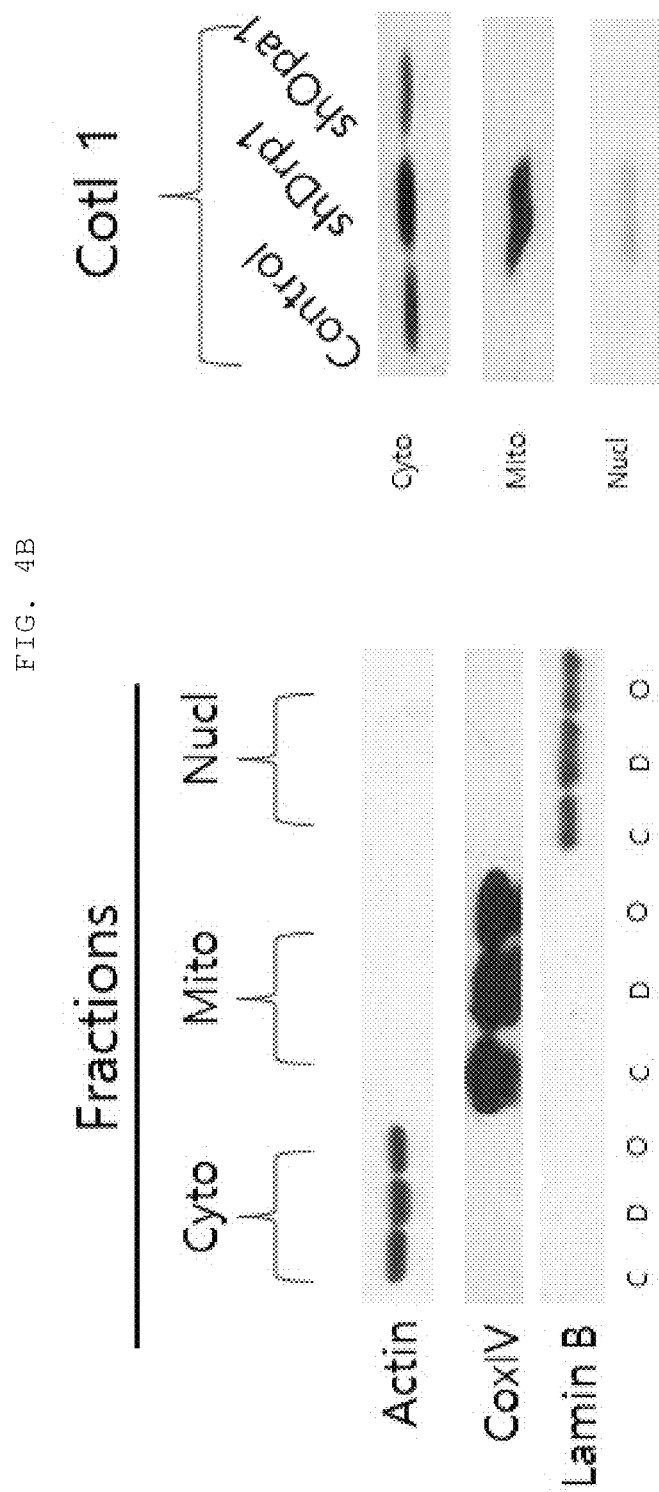

The intracellular distribution of COTL1 in the three types of cells having different mitochondrial lengths was analyzed in the nuclear, cytosolic and mitochondrial fractions. As a result, it was confirmed that, in the shDrp1 cells with an increased mitochondrial length, the COTL1 protein migrated much from the cytosol to the mitochondria (FIG. 4b).

2-2: Observation of Intracellular COTL1 Distribution by Immunofluorescence Microscopy In order to observe the cells with an immunofluorescence microscope, the cells were washed with phosphate buffered saline (PBS) and fixed with 4% formaldehyde (Electron Microscopy Sciences) at room temperature for 20 minutes. The cells were permeated with 0.1% Triton X-100 for 30 minutes and incubated with 10% FBS-containing blocking buffer for 1 hour. The sample was incubated with anti-Cotl1 primary antibody (Abcam, T3481) in blocking buffer at room temperature for 2 hours, and then washed with PBS and incubated with secondary antibody at room temperature for 2 hours. After incubation with the secondary antibody, 500 nM Alex Fluor 568 Phallaoidin (Invitrogen), Alex Fluor 350 Phalloidin (Invitrogen) or MitoTracker Red CMXRos (Invitrogen) was used, if necessary, and the sample was stained or not stained with DAPI (Invitrogen) and was mounted on VECTASHIELD.

Figure 4C:
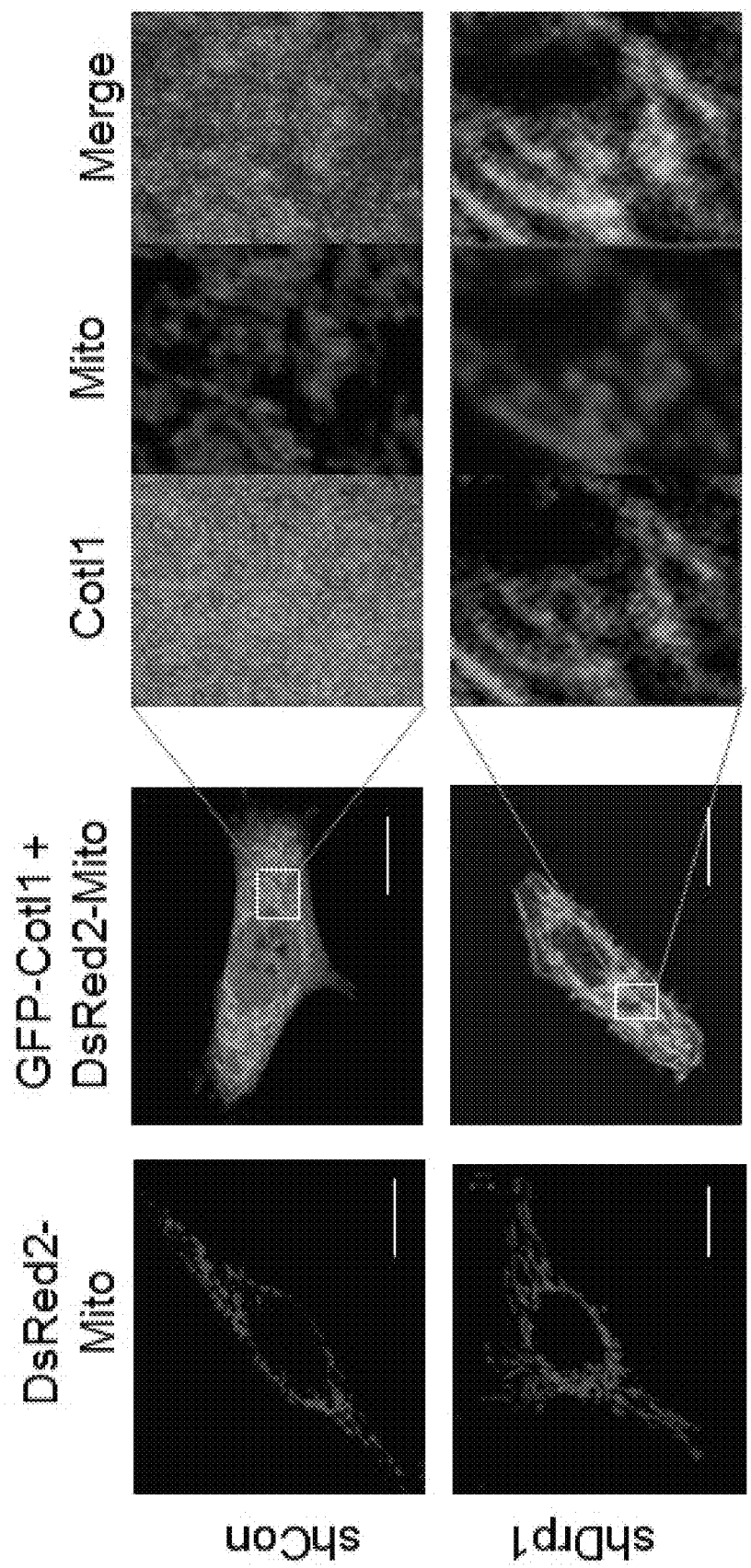

The confocal microscope images were analyzed, and as a result, it was confirmed that, in the shDrp1 cells with an increased mitochondrial length, the COTL1 protein migrated much from the cytosol to the mitochondria (FIG. 4c).

Example 3: Mitochondrial Morphology by F-Actin Binding to COTL1

3-1: F-Actin by COTL1 Knockdown

It was reported that COTL1 binds to various types of actin proteins that regulate the cytoskeleton, and particularly, bind primarily to F-actin. In addition, such actin proteins that form the cytoskeleton are involved in regulating a balance between mitochondrial fusion and fission. Thus, the effect of F-actin by abnormalities of COTL1 on mitochondrial morphology was analyzed.

Figure 5A:
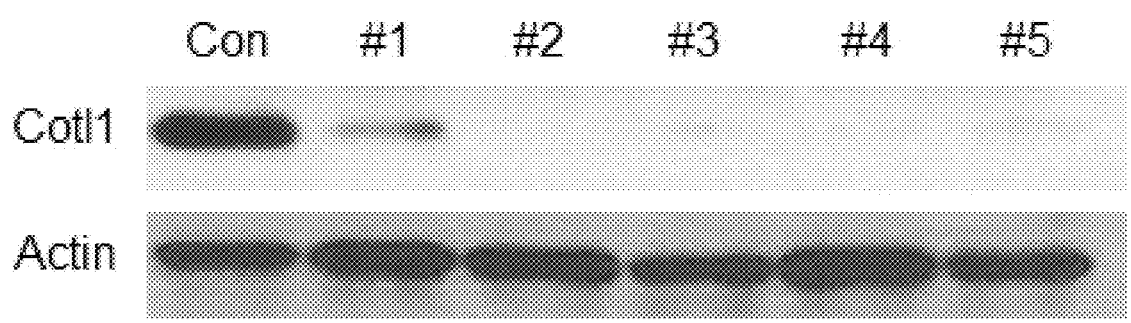
FIGS. 5A to 5C show the abnormal changes in the morphology of F-actin by mutation or knockdown of COTL1, as well as the distribution of F-actin in mitochondria and changes in the morphology of mitochondria.

First, knockdown of the COTL1 gene was induced using a lentivirus inserted with short hairpin RNA (shRNA), and the gene was analyzed by Western blotting (FIG. 5a).

A Mission shRNAi vector (RNAi #1; TRCN0000072549, RNAi #2; TRCN0000072550, RNAi #3; TRCN0000291958, RNAi #4; TRCN0000292021, RNAi #5; TRCN0000310158) for down-regulating Cotl1 was purchased from Sigma-Aldrich, and a pCDH-CMV-MCS-T2A-puro lentivirus expression vector was purchased from System Biosciences. Oligonucleotides for human total Opa1 and Drp1 were synthesized by IDT Oligo against target sequences 5'-GAUGAAGUUAUCAGUCUGAGCCAG-GUUAC-3' (Opa1: SEQ ID NO: 1) and 5'-UU-CAAUCCGUGAUGAGUAUGCUUUUCUUC-3' (Dpr1: SEQ ID NO: 2).

Cells were re-suspended in SDS-PAGE buffer and boiled at 100° C. for 5 minutes, and then the protein was analyzed on 8 to 12% polyacrylamide gel and transferred to a PVDF membrane (polyvinylidine difluoride membrane, Millipore), followed by SDS-PAGE. The membrane was blocked with 5% (w/v) nonfat dry milk or BSA for 1 hour. Next, the membrane was incubated with primary antibody overnight at 4° C., washed with PBS/0.1% Tween-20, incubated with secondary antibody at room temperature for 1 hour, and visualized with a WEST-ZOL plus ECL Western blot detection system (iNtRON BioTechnology).

3-2: F-Actin by COTL1 Mutation

Figure 5B:
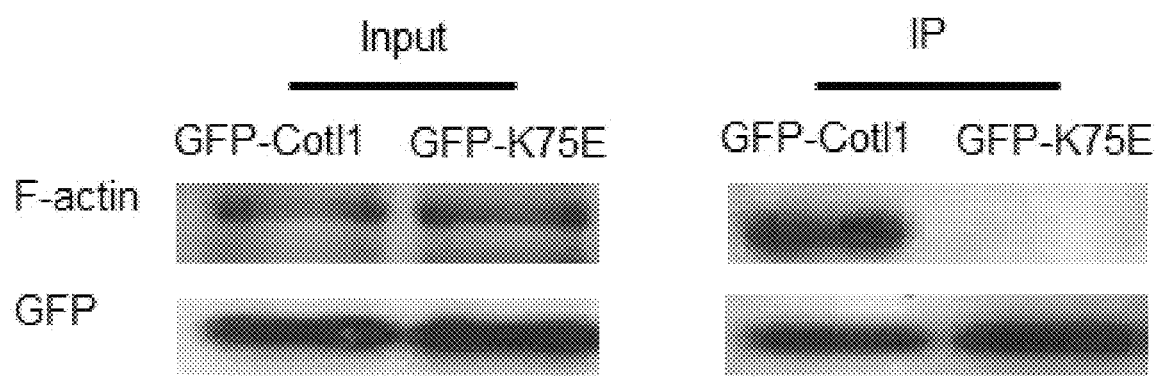

A COTL1 R75E mutation that does not bind to F-actin was constructed and analyzed by immunoprecipitation (IP) (FIG. 5b).

For immunoprecipitation (IP), cells were lysed in RIPA buffer (150 mM NaCl, 1% Nonidet P-40, 0.5% sodium deoxycholate, 0.1% SDS and 50 mM Tris buffer, pH 8.0) at 4° C., and the cell lysate was centrifuged at 13000 rpm and 4° C. for 20 minutes. The supernatant was collected and precleared with protein A Sepharose beads (GE Biosciences) at 4° C. for 2 hours. 2 µg of appropriate antibody was added thereto and incubated in a cold room overnight, and the immune complexes bound to protein A sepharose beads were collected.

Figure 5C:
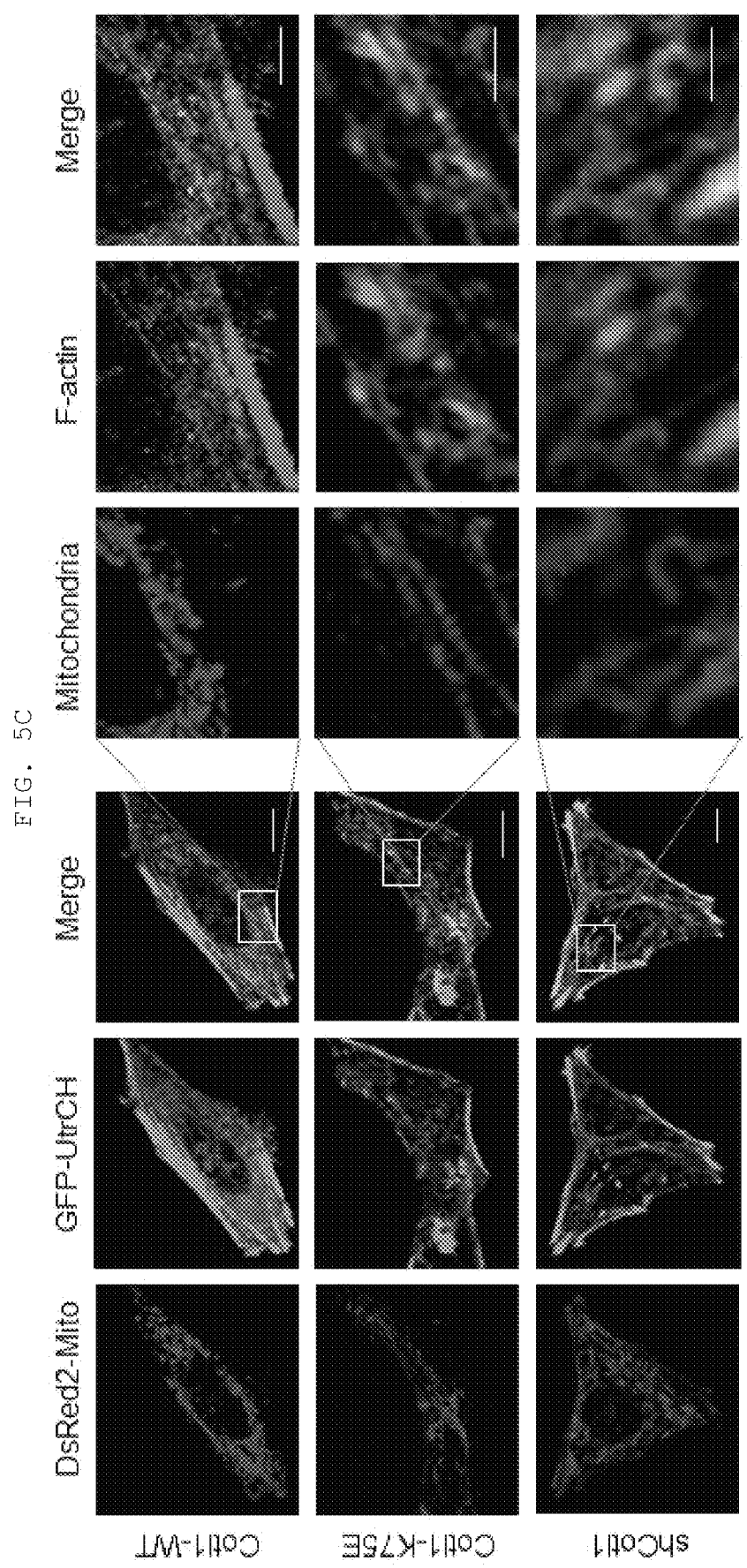

As a result, it was confirmed that when COTL1 was knocked down or the COTL1 R75E mutation was overexpressed, the abnormal morphology of F-actin appeared, and the distribution of F-actin in mitochondria increased and the length of mitochondria also increased (FIG. 5c). Accordingly, it could be seen that COTL1 influenced mitochondrial dynamics by regulating the morphology of F-actin.

Example 4: Expression Level and Distribution of Cotl1 in Zebrafish

Since human COTL1 and zebrafish cotl1 had a high amino acid sequence similarity of 81%, it can be seen that the COTL1 gene/protein is well conserved between biological species. Thus, through an animal experiment, phenomena occurring when the COTL1 gene is knocked down were observed.

In order to observe the expression level and distribution of cotl1 (which is a gene homologous to human COTL1) in zebrafish, wild-type (WT) zebrafish (AB strain) was obtained from the Zebrafish International Resource Center (Eugene, OR), and then managed according to standard procedures (Westerfield M. *THE ZEBRAFISH BOOK: A guide for the laboratory use of zebrafish* (Danio rerio). 5 ed: University of Oregon Press, 2007) and staged to hours post-fertilization (hpf) or days post-fertilization (dpf) according to standard criteria. To inhibit melanin synthesis, the embryo was treated with 1-phenyl-2-thiourea (Sigma-Aldrich, MO). In the zebrafish developmental stage, the expression of cotl1 was analyzed by in situ hybridization.

First, zebrafish total RNA was extracted from 2 dpf WT larvae using Trizol (Thermo Fisher, MA) and converted into cDNA using a SuperScript III First-Strand Synthesis System (Thermo Fisher) (Lim H S et al., *Chonnam Med J* 52:45-52, 2016). Zebrafish cotl1 was amplified by PCR using the cDNA and primers (SEQ ID NO: 3: 5'-TCG GCG GAT CCA CCA TGG CAA CAC GAA TTG AC-3' and SEQ ID NO: 4: 5'-TAG TC C TCG AGT TAT TCA GCC TGG GCA TC-3'). The amplified PCR product was cloned into the BamHI/XhoI sites of a pCS4+plasmid (provided by Chang-Yeol Yeo; Jin Y H et al., *J Biol Chem* 279:29409-17, 2004), and the constructed plasmid was confirmed by DNA sequencing (Macrogen, Korea). To produce cotl1 riboprobes, the constructed pCS4+plasmid encoding cotl1 or c-myb was linearized with BamHI, and then transcribed into RNA in vitro by using T7 RNA polymerase (Thermo Fisher) and a DIG RNA Labeling Kit (Roche, Switzerland). In situ hybridization was performed according to a previously described method (Kim K H et al., *Aquat Toxicol* 134-135:57-65, 2013) using cotl1 or c-myb riboprobes, and images were taken with a V20 stereomicroscope (Zeiss, Germany), and then merged using Adobe Photoshop CS6 (San Jose, CA).

Figure 6:
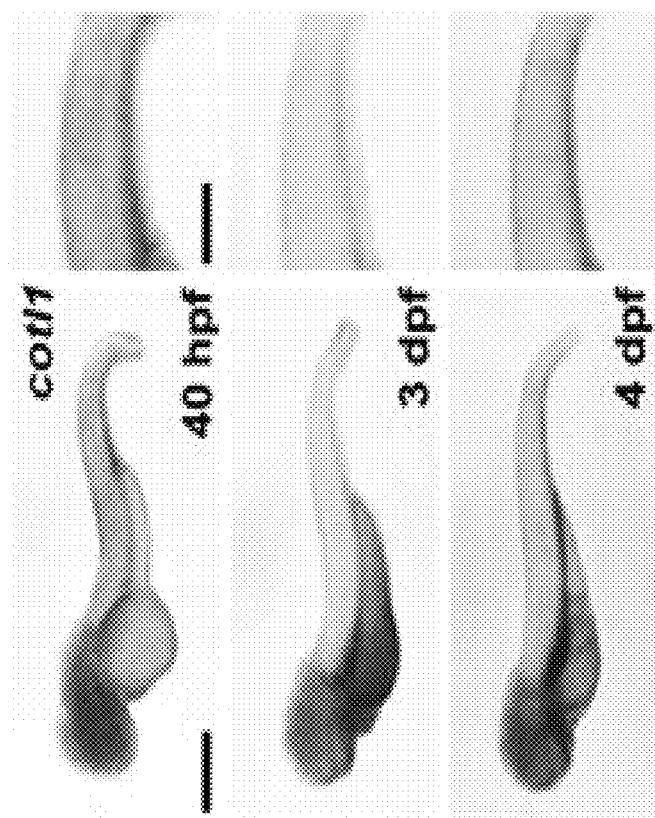
FIG. 6 shows the expression level and distribution of cotl1 in the zebrafish developmental stage.

As a result, it was confirmed that cotl1 was much expressed in the hematopoietic system, the gastrointestinal tract and the brain at 40 hours after fertilization (40 hpf) and on 3 and 4 days after fertilization (FIG. 6).

Example 5: Cotl1 Knockdown in Zebrafish 5-1: Morpholino (MO) RNA for Cotl1 Knockdown In order to knockdown cotl1 in zebrafish, morpholino (MO) RNA was used.

A cotl1 morpholino oligonucleotide (cotl1 MO) (SEQ ID NO: 5: 5'-CAA GAC AGG TAA ACA GCA CTC ACC T-3') targeting the exon 2-intron 2 junction of cotl1 was purchased from Gene Tools (OR). One-cell stage embryos were injected with control MO (6 ng; SEQ ID NO: 6: 5'-CCT CTT ACC TCT GTT ACA ATT TAT A-3') or cotl1 MO (6 ng) and incubated in embryo medium at 28.5° C. embryo medium until they were fixed at indicated stages. To synthesize cotl1 mRNA, the pCS4+plasmid encoding cotl1 was linearized with XhoI, and then transcribed into RNA in vitro by a SP6 mMESSAGE mMACHINE kit (Thermo Fisher) according to the manufacturer's instruction. Next, cotl1 MO (6 ng) and cotl1 mRNA (70 pg) were sequentially injected into the one-cell stage embryos, and the injected embryos were incubated until 2 dpf, and then probed with c-myb riboprobes.

FIG. 7 shows the results of analyzing the position of morpholino (MO) RNA and the expression of RNA.

5-2: Decrease in Number of Hematopoietic Stem Cells by Cotl1 Knockdown

In order to confirm whether cotl1 is knocked down in transformed zebrafish, reverse transcription PCR was performed (FIG. 8a).

Total RNA was extracted from the larvae injected with control MO or cotl1 MO, and was reverse-transcribed into cDNA using a SuperScript III First-Strand Synthesis System (Thermo Fisher). RT-PCR was performed by amplifying the cDNA fragment including exons 1 to 4 by PCR using primers (SEQ ID NO: 7: 5'-GAC AAA GAG GCT TGC AGA GA-3' and SEQ ID NO: 8: 5'-TGG GGT CGC TGA TCA TAA AC-3').

Figure 8B:

In addition, from the expression of the hematopoietic stem cell detection marker c-myb, analyzed using the in situ hybridization method of Example 4, it was confirmed that the number of hematopoietic stem cells in cotl1 MO RNA-treated zebrafish on 2 days post-fertilization (2 dpf) significantly decreased, and the number of hematopoietic stem cells injected with cotl1 MO RNA along with cotl1 RNA did not greatly differ from that in the control (FIG. 8a). In addition, it was confirmed that, even in transformed zebrafish that expresses GFP (green florescence protein) only in hematopoietic stem cells, cotl1 knockdown resulted in a significant decrease in the number of hematopoietic stem cells (FIG. 8b).

Example 6: Cotl1 Knockdown in Mice 6-1: Cotl1-Knockdown Mice

Cotl1-knockdown mice were obtained from the International Mouse Phenotyping Consortium, and rederived mice with cotl1-knockout frozen embryonic stem cells were received and raised. In an animal testing center, wild-type, heterozygote, and homozygote cotl1 knockout mouse models were constructed.

6-2: Analysis of Blood of Cotl1-Knockdown Mice

Using 12-week-old and 24-week-old wild-type and homozygote mice (3 males and 3 females), blood analysis was performed. After anesthetizing the mice, the abdomen was opened, and then blood was collected from the right heart and analyzed.

From the results of the analysis, it was confirmed that PLT (platelet) counts (FIG. 9) and WBC (white blood cell) counts (FIG. 10) in the male and female homozygote mice decreased compared to those in the wild-type mice. Particularly, it was confirmed that PLT counts and WBC counts significantly decreased in the 24-week-old male and female homozygote mice.

INDUSTRIAL APPLICABILITY

The COTL1 gene or protein of the present invention plays an important role in regulating mitochondrial morphology, and when it is knocked down, the number of hematopoietic stem cells decreases. Thus, the COTL1 gene or protein is useful for the diagnosis and treatment of blood-related disease caused either by abnormalities in the homeostasis of hematopoietic stem cells, or by an imbalance between the differentiation or proliferation and damage or death of hematopoietic stem cells, or by abnormalities in mitochondrial homeostasis.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for treating a blood-related disease in a subject in need thereof, the method comprising administering to the subject an effective amount of an inhibitor of expression of COTL1 protein,
wherein the blood-related disease is a leukemia caused by an increase in abnormal proliferation of hematopoietic stem cells, and the treating comprises a decrease in a number of hematopoietic stem cells compared to prior to the administering,
wherein the administering reduces a number of hematopoietic stem cells, and
wherein the inhibitor is any one selected from the group consisting of an antisense nucleotide, a small interfering RNA (siRNA), and a short hairpin RNA (shRNA), which each bind complementarily to the mRNA of the COTL1 gene, and a combination thereof,
wherein the inhibitor is a morpholino oligonucleotide comprising the sequence of SEQ ID: 5.

2. The method of claim 1, wherein the blood-related disease is selected from the group consisting of acute myeloid leukemia, acute lymphoblastic leukemia, chronic myeloid leukemia, and chronic lymphocytic leukemia.

3. The method of claim 1, wherein the blood-related disease is caused by i) abnormalities in the homeostasis of hematopoietic stem cells, ii) an imbalance between the differentiation or proliferation and damage or death of hematopoietic stem cells, or iii) abnormalities in mitochondrial homeostasis.

* * * * *